United States Patent
Spengler

(10) Patent No.: US 6,692,765 B1
(45) Date of Patent: Feb. 17, 2004

(54) EXACTLY DIVISIBLE TABLET

(75) Inventor: Reinhard Spengler, Maxdorf (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/762,399

(22) PCT Filed: Aug. 11, 1999

(86) PCT No.: PCT/EP99/05905

§ 371 (c)(1),
(2), (4) Date: Feb. 7, 2001

(87) PCT Pub. No.: WO00/10535

PCT Pub. Date: Mar. 2, 2000

(30) Foreign Application Priority Data

Aug. 19, 1998 (DE) .......................... 198 37 684

(51) Int. Cl.⁷ ................................. A61K 9/44
(52) U.S. Cl. ...................... 424/467; D24/103
(58) Field of Search ......................... 424/467; D24/103

(56) References Cited

U.S. PATENT DOCUMENTS

| D201,497 S | * | 6/1965 | Ninger | D24/103 |
| 3,336,200 A | | 8/1967 | Krause | 424/465 |
| 4,258,027 A | * | 3/1981 | Ullman et al. | 424/467 |
| D383,535 S | * | 9/1997 | Bryan, Jr. et al. | D24/103 |

FOREIGN PATENT DOCUMENTS

| DE | 1 200 790 | | 9/1965 |
| DE | 1 492 237 | | 9/1969 |
| EP | 0207 888 | * | 5/1986 |
| EP | 207 888 | | 1/1987 |
| JP | 7-179333 | * | 7/1995 |

* cited by examiner

Primary Examiner—Thurman K. Page
Assistant Examiner—Frank Choi
(74) Attorney, Agent, or Firm—Wood, Phillips, Katz, Clark & Mortimer

(57) ABSTRACT

The invention describes a tablet with two end faces and a circumferential face, in which the mutually opposite end faces of the tablet a) overall are nonplanar and are arranged at least approximately parallel to one another, and b) are each provided with a score on the top and bottom sides, the scores lying in the center of the tablet parallel to and above one another.

2 Claims, 1 Drawing Sheet

EXACTLY DIVISIBLE TABLET

Figure 1:
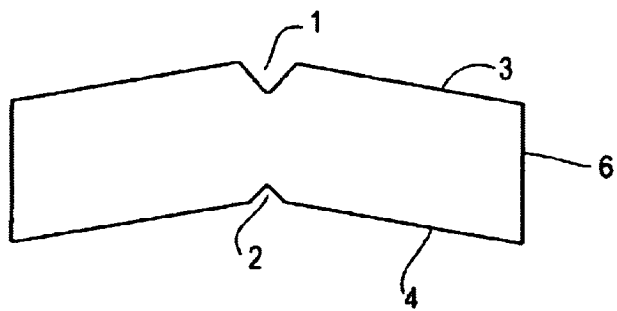

This application is a 371 of PCT/EP99/05905, filed Aug. 11, 1999.

The present invention relates to a tablet which can be divided exactly.

Virtually all tablets which contain pharmaceutically active compounds can be made manually divisible by appropriately selecting the size and shape and by forming one or more scores. However, tablets which are currently known either can only be divided in one direction, which often causes problems for older patients, or cannot be divided into tablet halves which contain the same amount of active compound. According to a proposal made by the European Pharmacopoeia Commission (Report 96th Meeting), the weight contents of the active compounds in the tablet halves should differ by no more than 10% by mass when the complete tablet contains more than 250 mg of active compound and by no more than 15% by mass when the complete tablet contains less than 250 mg of active compound. Since, according to the German Pharmacopoeia (10th Edition), the active compound content alone in the individual tablets may, depending on the amount of active compound desired and on the tablet size, differ by 5 to 10% from the desired value, the administration of divided tablets may result in problems caused by fluctuations in the amount of active compound administered.

A tablet has now been discovered which can be divided in two directions and which when divided breaks into two halves which contain substantially the same amount of active compound.

The invention relates to a tablet with two end faces and a circumferential face, wherein the mutually opposite end faces of the tablet a) overall are nonplanar and are arranged at least approximately parallel to one another, and b) are each provided with a score on the top and bottom sides, the scores lying in the center of the tablet parallel to and above one another.

The mutually opposite end faces of the tablet preferably lie parallel or approximately parallel to one another. The two halves of the tablet should form an angle of from 130 to 177°. For small tablets, this angle will preferably lie closer to 130°, while for larger tablets it may be up to 177°. It must in any case be sufficiently great for the tablet to break correctly when pressure is applied to the top or bottom side. The mutually opposite end faces preferably run parallel to one another. For relatively large tablets, the angle which the bottom end face (cf. FIG. 3) forms may be somewhat smaller (i.e. up to 25°, preferably up to 15°) if it is desired to increase the volume of the tablet without affecting the breaking properties.

The depth of the scores is generally from 5 to 10% of the tablet thickness at the score. There are no particular requirements for the shape of the scores.

It is expedient to provide the tablets, at the edges, on the top or bottom side, preferably on both sides, with a phase [sic] (=facet, slope), so that the load which the ram can apply when pressing the tablet is increased. If the tablet has one phase [sic] on the top and bottom sides, these phases [sic] are preferably offset by approximately 90° with respect to one another.

The tablets are normally round, but may also be oval (for example oblong) or polygonal (for example rectangular or square), in which case the corners are rounded. The diameter of the tablets should be from at least 4 mm to 14 mm if they are for oral administration.

The novel tablet has the following advantages:

1. The tablet can easily be divided when placed on a surface by applying pressure from above (for example using a finger). When doing so, it is irrelevant which side of the tablet lies on the surface. This is particularly important if the tablet is to be broken by someone who has difficulty seeing.

2. The loss of tablet material when breaking the tablet is minimal.

3. The standard deviation of the mass of the pieces is <3%.

4. The tablet has a suitably high resistance to breaking, which is important for subsequent pharmaceutical working steps in which the tablet has to combine a certain level of strength with an advantageously low breaking force.

5. The fact that the tablet has substantially planar faces at its surface means that imprints for identifying the tablet can easily be applied without causing any damage to the tablet, even at high tabletting rates. On curved surfaces, this can only be carried out with a much greater level of outlay.

6. The crescent-shaped facet allows the novel tablet to slide out of the press mold used in the tabletting process particularly easily, so that there is no damage to the tablet when it is ejected even at relatively high pressing rates.

The figures show particular embodiments of the invention.

FIG. 1 shows a cross section through a tablet. 1 and 2 are the scores, 3 is the top end face and 4 is the bottom end face, while 6 is the circumferential face of the tablet.

Figure 2:
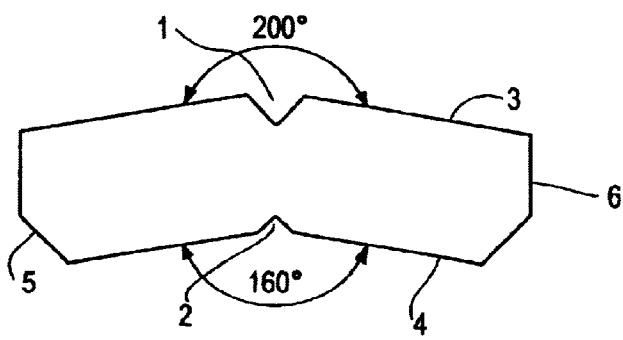

FIG. 2 shows a cross section through a tablet in accordance with FIG. 1, on which a phase [sic] 5 is additionally formed.

Figure 3:
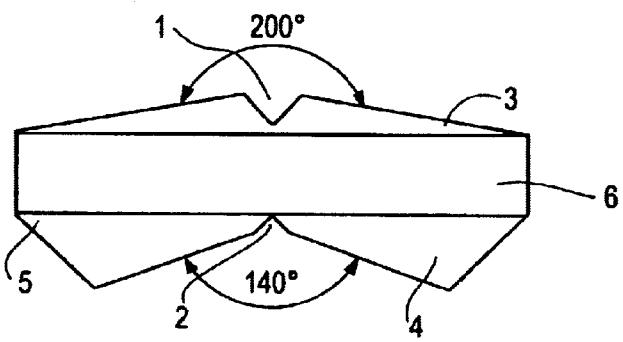

FIG. 3 corresponds to FIG. 2, but with the bottom end face more angled.

Figure 4:
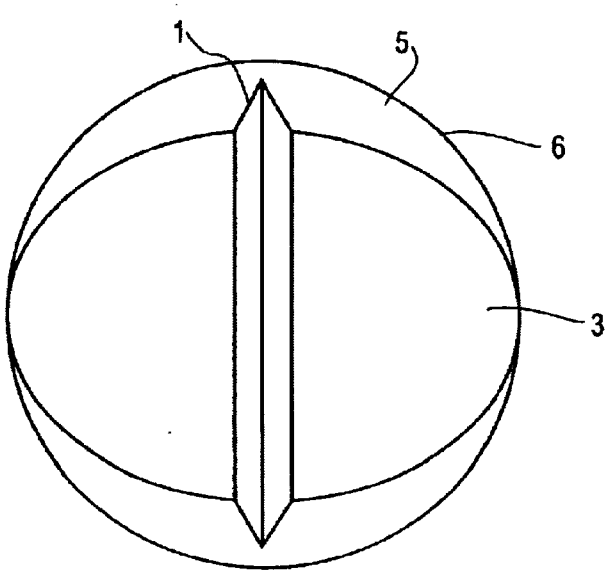

FIG. 4 shows a view of the tablet shown in FIG. 2. 1 denotes a score, 3 denotes the top end face with the phase [sic] 5.

I claim:

1. A tablet with two end faces and a circumferential face, wherein the mutually opposite end faces of the tablet a) overall are non-planar and are arranged at least approximately parallel to one another, and b) are each provided with a score on the top and bottom sides, the scores lying in the center of the tablet parallel to and above one another, wherein the tablet is provided at the edges, on the top and bottom side, with in each case two crescent-shaped phases that are offset by approximately 90° with respect to one another.

2. A tablet as claimed in claim 1, wherein the tablet halves which are divided by the score form an angle of from 130 to 177°.

* * * * *